United States Patent

Brooks et al.

[11] Patent Number: 5,840,758
[45] Date of Patent: Nov. 24, 1998

[54] OXIME DERIVATIVES OF FENAMATES AS INHIBITORS OF PROSTAGLANDIN BIOSYNTHESIS

[75] Inventors: Clint D. W. Brooks, Libertyville; Teodozyj Kolasa, Lake Villa, both of Ill.; Wendy Lee, Hamden, Conn.; Andrew O. Stewart, Libertyville, Ill.

[73] Assignee: Abbott Laboratories, Abbott Park, Ill.

[21] Appl. No.: 659,474

[22] Filed: Jun. 6, 1996

[51] Int. Cl.⁶ .................. A61K 31/41; A61K 31/275; A61K 31/19; A61K 31/165
[52] U.S. Cl. .................. 514/564; 514/381; 514/524; 514/539; 514/619; 514/620; 514/640; 514/824; 514/825; 514/863; 514/886; 514/887; 514/916; 548/252; 558/418; 560/35; 562/440
[58] Field of Search .................... 514/381, 524, 514/539, 569, 619, 620, 640, 824, 825, 863, 886, 887, 916; 548/252; 558/418; 560/35; 562/440; 564/163, 164, 165, 167, 253, 256

[56] References Cited

U.S. PATENT DOCUMENTS 5,446,067  8/1995  Benoit et al. .......................... 564/256

*Primary Examiner*—Peter O'Sullivan
*Attorney, Agent, or Firm*—Frank Z. Yang

[57] ABSTRACT

Compounds having the formula

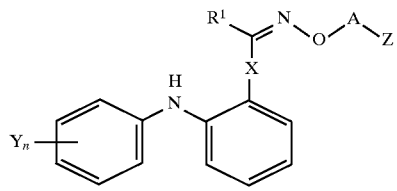

or a pharmaceutically acceptable salt thereof wherein Y is selected from halogen, alkyl, and haloalkyl; n is 0, 1, 2, or 3; A is selected from (a) optionally substituted alkylene, (b) optionally substituted cycloalkylene, (c) optionally substituted cycloalkylene wherein one or two of the carbon atoms is replaced with one or two heteroatoms independently selected from O, S, and N, (d) optionally substituted alkenylene and (e)

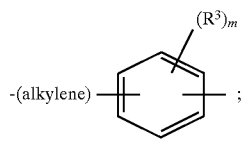

X is absent or is alkylene; Z is selected from (a) hydrogen, (b) COM wherein M is selected from —$OR^4$, —$NR^6R^7$, and a pharmaceutically acceptable metabolically cleavable group, (c) —$OR^2$, (d) tetrazolyl, (e) —$CH(OR^2)$—$CH_2OR^8$, (f) —$CH(OR^2)$—$CH_2$—$CH_2OR^8$, (g) —$CH(OR^2)$—$CH(OR^8)$—$CH_2OR^9$, and (h)=N—$OR^2$; and $R^1$ is selected from hydrogen, alkyl, and optionally substituted phenyl, are prostaglandin biosynthesis inhibitors and are useful in the treatment of inflammatory disease states. Also disclosed are prostaglandin inhibiting compositions, a method of inhibiting prostaglandin biosynthesis in a mammal.

13 Claims, No Drawings

OXIME DERIVATIVES OF FENAMATES AS INHIBITORS OF PROSTAGLANDIN BIOSYNTHESIS

TECHNICAL FIELD

This invention relates to novel compounds having activity to inhibit prostaglandin biosynthesis, to pharmaceutical compositions comprising these compounds and to a medical method of treatment. More particularly, this invention concerns oxime containing derivatives of fenamate compounds which inhibit prostaglandin biosynthesis particularly the induced prostaglandin endoperoxide H synthase (PGHS-2, cyclooxygenase-2, COX-2), to pharmaceutical compositions comprising these compounds and to a method of inhibiting prostaglandin biosynthesis.

BACKGROUND OF THE INVENTION

The prostaglandins are extremely potent substances which produce a wide variety of biological effects, often in the nanomolar to picomolar concentration range. The discovery of two forms of prostaglandin endoperoxide H synthase, PGHS-1 and PGHS-2, that catalyze the oxidation of arachidonic acid leading to prostaglandin biosynthesis has resulted in renewed research to delinate the role of these two isozymes in physiology and pathophysiology. These isozymes have been shown to have different gene regulation and represent distinctly different prostaglandin biosynthesis pathways. The PGHS-1 pathway is expressed constitutively in most cell types. It responds to produce prostaglandins that regulate acute events in vascular homeostasis and also has a role in maintaining normal stomach and renal function. The newly discovery PGHS-2 pathway involves an induction mechanism which has been liked to inflammation, mitogenesis and ovulation phenomena.

Prostaglandin inhibitors provide therapy for pain, fever, and inflammation, and are useful therapies, for example in the treatment of rheumatoid arthritis and osteoarthritis. The non-steroidal antiinflammatory drugs (NSAIDs) such as ibuprofen, naproxen and fenamates inhibit both isozymes, prostaglandin endoperoxide H synthase 1 (PGHS-1) and prostaglandin endoperoxide H synthase 2 (PGHS-2). Inhibition of the constitutive enzyme PGHS-1 results in gastrointestinal side effects including ulcers and bleeding and incidence of renal problems with chronic therapy. Inhibitors of the induced isozyme PGHS-2 are proposed to provide antiinflammatory activity without the side effects of PGHS-1 inhibitors. A general review of the current knowledge of PGHS-1 and PGHS-2 isozyme properties and a summary of inhibitors and their activity is provided by:

(1) Battistini, B.; Botting, R.; Bakhle, Y. S. COX-1 and COX-2: toward the development of more selective NSAIDs, Drug New and Perspectives 1994, 7(8), 501–512.

(2) DeWitt, D. L.; Bhattacharyya, D.; Lecomte, M.; Smith, W. L. The differenctial susceptibility of prostaglandin endoperoxide H synthases-1 and -2 to non-steroidal anti-inflammatory drugs: aspirin derivatives as selective inhibitors. Med. Chem. Res. 1995, 5(5), 325–343.

(3) Mitchell, J. A.; Larkin, S.; Williams, T. J. Cyclooxygenase-2: regulation and relevance in inflammation. Biochem. Pharm. 1995, 50(10), 1535–1542.

Fenamate compounds were developed as prostaglandin biosynthesis inhibitors prior to the discovery of the different isozyme forms. The reported fenamates (Scherrer, R. A. Fenamic acids, in "Anti-inflammatory and anti-rheumatic drugs", Vol II, Rainsford, K. D. ed., CRC Press, Boca Raton, Fla., 1985, Chapter 4, pp 65–85) include: diclofenac, meclofenamic acid, mefenamic acid, flufenamic acid, and tolfenamic acid. Meclofenamic acid, a representative fenamate NSAID, has been reported to inhibit both PGHS-1 and PGHS-2 (Battistini, B.; Botting, R.; Bakhle, Y. S. COX-1 and COX-2: toward the development of more selective NSAIDs, Drug New and Perspectives 1994, 7(8), 501–512.)

SUMMARY OF THE INVENTION

In its principal embodiment, the present invention provides certain novel oxime containing derivatives of fenamate compounds with unexpected preferrential inhibitory activity against the induced PGHS-2 isozyme versus PGHS-1 which are useful in the treatment of allergic and inflammatory disease states in which the prostaglandins play a role.

The compounds of the present invention have the formula

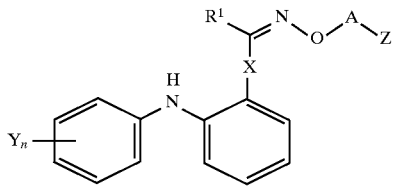

or a pharmaceutically acceptable salt thereof wherein Y is selected from the group consisting of halogen, alkyl of one to six carbon atoms, and haloalkyl of one to six carbon atoms, and n is 0, 1, 2,or3.

A is selected from the group consisting of (a) alkylene of one to six carbon atoms, (b) alkylene of one to six carbon atoms substituted with one or two substituents selected from the group consisting of $-OR^2$, $-CN$, $-NO_2$, and $-COOR^2$, (c) cycloalkylene of three to eight carbon atoms, (d) cycloalkylene of three to eight carbon atoms substituted with one or two substituents independently selected from alkyl of one to six carbon atoms, $-OR^2$, $-CN$, $-NO_2$, and $-COOR^2$, (e) cycloalkylene of three to eight carbon atoms wherein one or two of the carbon atoms is replaced with one or two heteroatoms independently selected from O, S, and N, (f) cycloalkylene of three to eight carbon atoms wherein one or two of the carbon atoms is replaced with one or two heteroatoms independently selected from O, S, and N, and the ring contains one or two substituents independently selected from alkyl of one to six carbon atoms, $-OR^2$, $-CN$, $-NO_2$, and $-COOR^2$, (g) alkenylene of two to six carbon atoms, (h) alkenylene of two to six carbon atoms substituted with one or two substituents selected from the group consisting of $-OR^2$, $-CN$, $-NO_2$, and $-COOR^2$, (i)

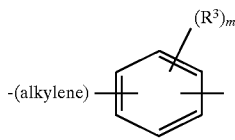

wherein m is 0, 1, 2, or 3, and $R^3$, which may by the same or different at each occurrence, is selected from the group consisting of $-OR^2$, $-CN$, $-NO_2$, $-COOR^2$, halogen, alkyl of one to six carbon atoms, haloalkyl of one to six carbon atoms, and alkoxy of one to six carbon atoms.

X is absent or is alkylene of one to six carbon atoms.

Z is selected from the group consisting of (a) hydrogen, (b) COM wherein M is selected from the group consisting of (b-1) —OR$^4$ wherein R$^4$ is selected from the group consisting of (b-1-a) a pharmaceutically acceptable cation, (b-1-b) hydrogen, (b-1-c) alkyl of one to six carbon atoms, (b-1-d) phenyl, (b-1-e) phenyl substituted one, two or three substituents selected from halogen, alkyl of one to six carbon atoms, haloalkyl of one to six carbon atoms, alkoxy of one to six carbon atoms, and

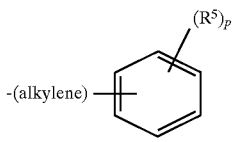

wherein p is 0, 1, 2, or 3, and R$^5$, which may by the same or different at each occurrence, is selected from halogen, alkyl of one to six carbon atoms, haloalkyl of one to six carbon atoms, and alkoxy of one to six carbon atoms, (b-2) —NR$^6$R$^7$ wherein R$^6$ and R$^7$ are independently selected from hydrogen, alkyl of one to six carbon atoms, hydroxyalkyl of one to six carbon atoms, and hydroxy; and (b-3) a pharmaceutically acceptable metabolically cleavable group, (c) —OR$^2$, (d) tetrazolyl, (e) —CH(OR$^2$)—CH$_2$OR$^8$, (f) —CH(OR$^2$)—CH$_2$—CH$_2$OR$^8$, (g) —CH(OR$^2$)—CH(OR$^8$)—CH$_2$OR$^9$, and (h) =N—OR$^2$.

R$^1$, R$^2$, R$^8$, and R$^9$ are independently selected at each occurrence from the group consisting of (a) hydrogen, (b) alkyl of one to six carbon atoms, (c) phenyl, (d) phenyl substituted one, two or three substituents selected from halogen, alkyl of one to six carbon atoms, haloalkyl of one to six carbon atoms, alkoxy of one to six carbon atoms, and

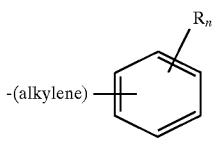

wherein m is 0, 1, 2, or 3, and R, which may by the same or different at each occurrence, is selected from halogen, alkyl of one to six carbon atoms, haloalkyl of one to six carbon atoms, and alkoxy of one to six carbon atoms.

In those instances where M=OH, the compounds of the present invention are capable of forming base addition salts. In such instances, the term "pharmaceutically acceptable salts" refers to the relatively nontoxic inorganic and organic base addition salts of compounds of the present invention. These salts can be prepared in situ during the final isolation and purification of the compounds, or by separately reacting the purified carboxyl compound with a suitable base such as the hydroxide, carbonate, or bicarbonate of a pharmaceutically acceptable metal cation or with ammonia, or an organic primary, secondary, or tertiary amine of sufficient basicity to form a salt with the carboxyl functional group of the compounds of this invention.

Representative alkali or alkaline earth metal salts include sodium, lithium, potassium, calcium, magnesium, and the like. Representative organic amines useful for the formation of base addition salts include ethylamine, diethylamine, ethylenediamine, ethanolamine, diethanolamine, piperazine, and the like. (See, for example, S. M Berge, et al., *J. Pharmaceutical Sciences*, 1977, 66: 1–19, which is incorporated herein by reference).

Similarly, in those instances where the compounds of the present invention contain a basic nitrogen atom, the compounds are capable of forming acid addition salts. In such cases, the term "pharmaceutically acceptable salts" refers to the relatively nontoxic inorganic and organic acid addition salts of compounds of the present invention. These salts can be prepared in situ during the final isolation and purification of the compounds, or by separately reacting the purified compound in its free-base form with a suitable inorganic or organic acid and isolating the salt thus formed. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. (See, for example, S. M Berge, et al., *J. Pharmaceutical Sciences*, 1977, 66: 1–19, which is incorporated herein by reference). Said pharmaceutically acceptable acid and base addition salts are also contemplated as falling within the scope of the present invention.

The present invention also provides pharmaceutical compositions which comprise a therapeutically effective amount of compound of claim 1 in combination with a pharmaceutically acceptable carrier.

The invention further relates to a method of inhibiting prostaglandin biosynthesis in a host mammal in need of such treatment comprising administering to a mammal in need of such treatment a therapeutically effective amount of a compound of claim 1.

DETAILED DESCRIPTION

Definitions of Terms

As used throughout this specification and the appended claims, the following terms have the meanings specified.

The term alkyl refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The terms alkoxy and alkoxyl denote an alkyl group, as defined above, attached to the parent molecular moiety through an oxygen atom. Representative alkoxy groups include methoxy, ethoxy, propoxy, butoxy, and the like.

The terms alkenyl as used herein refer to monovalent straight or branched chain groups of 2 to 6 carbon atoms containing a carbon-carbon double bond, derived from an alkene by the removal of one hydrogen atom and include, but are not limited to groups such as ethenyl, 1-propenyl, 2-propenyl, 2-methyl-1-propenyl, 1-butenyl, 2-butenyl and the like.

The term alkylene denotes a divalent group derived from a straight or branched chain saturated hydrocarbon containing by the removal of two hydrogen atoms, for example —CH$_2$—, —CH$_2$CH$_2$—, —CH(CH$_3$)CH$_2$— and the like.

The term aryl as used herein refers to a monovalent carbocyclic group containing one or more fused or non-fused phenyl rings and includes, for example, phenyl, 1- or 2-naphthyl, 1,2-dihydronaphthyl, 1,2,3,4-tetrahydronaphthyl, and the like.

The term cycloalkyl as used herein refer to a monovalent saturated cyclic hydrocarbon group. Representative cycloalkyl groups include cyclopropyl, cyclobutyl, cyclopentyl, cyclohexyl, cycloheptyl, bicyclo[2.2.1]heptane and the like.

Cycloalkylene denotes a divalent radical derived from a cycloalkane by the removal of two hydrogen atoms.

The term haloalkyl denotes an alkyl group, as defined above, having one, two, or three halogen atoms attached thereto and is exemplified by such groups as chloromethyl, bromoethyl, trifluoromethyl, and the like.

The term hydroxyalkyl represents an alkyl group, as defined above, substituted by one to three hydroxyl groups with the proviso that no more than one hydroxy group may be attached to a single carbon atom of the alkyl group.

As used throughout this specification and the appended claims, the term "metabolically cleavable group" denotes a moiety which is readily cleaved in vivo from the compound bearing it, which compound after cleavage remains or becomes pharmacologically active. Metabolically cleavable groups form a class of groups reactive with the carboxyl group of the compounds of this invention (where M is —OH) well known to practitioners of the art. They include, but are not limited to such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compouns of this invention are cleaved in vivo, the compounds bearing such groups act as pro-drugs of other prostanglandin biosynthesis inhibitors. The compounds bearing the metabolically cleavable groups have the advantage that they may exhibit improved bioavailability as a result of enhanced solubility and/or rate of absorption conferred upon the parent compound by virtue of the presence of the metabolically cleavable group.

By "pharmaceutically acceptable cation" it is meant those base addition salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable cations are well known in the art. For example, S. M Berge, et al. describe pharmaceutically acceptable salts in detail in *J. Pharmaceutical Sciences,* 1977, 66: 1–19. Representative pharmaceutically acceptable cations include alkali or alkaline earth metal cations such as sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

Asymmetric centers may exist in the compounds of the present invention. The present invention contemplates the various stereoisomers and mixtures thereof. Individual stereoisomers of compounds of the present invention are made by synthesis from starting materials containing the chiral centers or by preparation of mixtures of enantiomeric products follwed by separation as, for example, by conversion to a mixture of diastereomers followed by separation by recrystallization or chromatographic techniques, or by direct separation of the optical enantiomers on chiral chromatographic columns. Starting compounds of particular stereochemistry are either commercially available or are made by the methods detailed below and resolved by techniques well known in the organic chemical arts Preferred Embodiments Compounds contemplated as falling within the scope of the present invention include, but are not limited to 2-[(2,6-dichloro-3-methylphenyl)amino]benzaldehyde-O-carboxymethyl oxime, 2-[(2,6-dichloro-3-methylphenyl)amino]benzaldehyde-O-(3-carboxyethyl) oxime, 2-[(2,6-dichloro-3-methylphenyl)amino]benzaldehyde-O-(2-hydroxyethyl) oxime, 2-[(2,6-dichloro-3-methylphenyl)amino]benzaldehyde-O-(3-hydroxypropyl) oxime, 2-[(2,6-dichloro-3-methylphenyl)amino]benzaldehyde-O-[1-(2,3-dihydroxypropyl)] oxime, 2-[(2,6-dichloro-3-methylphenyl)amino]benzaldehyde-O-(5-tetrazolylmethyl) oxime, 2-[(2,6-dichloro-3-methylphenyl)amino]benzaldehyde-O-(aceto-2-hydroxyethylamide) oxime, 2-[(2,6-dichloro-3-methylphenyl)amino]benzaldehyde-O-(acetohydroxamic acid) oxime, 2-[(2,6-dichloro-3-methylphenyl)amino]phenyl}acetophenone-O-carboxymethyl oxime, 2-{[(2,6-dichloro-3-methylphenyl)amino]phenyl} phenyl ketone-O-carboxymethyl oxime, 2-[(2,6-dichloro-3-methylphenyl)amino]phenylmethyl ketone-O-carboxymethyl oxime, 2-[2-[(2,6-dichlorophenyl)amino]phenyl]acetaldehyde-O-carboxymethyl oxime, 2-[2-[(2,6-dichlorophenyl)amino]phenyl]acetaldehyde-O-carboxyethyl oxime, 2-[2-[(2,6-dichlorophenyl)amino]phenyl]acetaldehyde-O-(2-hydroxyethyl) oxime, 2-[2-[(2,6-dichlorophenyl)amino]phenyl]acetaldehyde-O-(3-hydroxypropyl) oxime, 2-[2-[(2,6-dichlorophenyl)amino]phenyl]acetaldehyde-O-[1-(2,3-dihydroxypropyl) oxime, 2-[2-[(2,6-dichlorophenyl)amino]phenyl]acetaldehyde-O-(5-tetrazolylmethyl) oxime, 2-[2-[(2,6-dichlorophenyl)amino]phenyl]acetaldehyde-O-(acetohydroxamic acid) oxime,

[2-[(2,6-dichlorophenyl)amino]benzyl]methyl ketone-O-carboxymethyl oxime,

2-[(3-chloro-2-methylphenyl)amino]benzaldehyde-O-carboxymethyl oxime,

2-[(2,3-dimethylphenyl)amino]benzaldehyde-O-carboxymethyl oxime,

2-[(3-trifluoromethylphenyl)amino]benzaldehyde-O-carboxymethyl oxime, and

2-[(2,6-dichloro-3-methylphenyl)amino]benzaldehyde-O-(2-acetaldehyde oxime) oxime.

Preferred compounds of the present invention have the structure described above wherein A is alkylene of one to six carbon atoms and Z is selected from the group consisting of —CH(OH)—CH$_2$OH, —CH(OH)—CH$_2$—CH$_2$OH, and —CH(OH)—CH(OH)—CH$_2$OH.

More preferred compounds have the structure described above wherein A is alkylene of one to six carbon atoms, and Z is —COOR$^4$ wherein R$^4$ is hydrogen or a pharmaceutically acceptable cation.

Still more preferred compounds are selected from the group consisting of

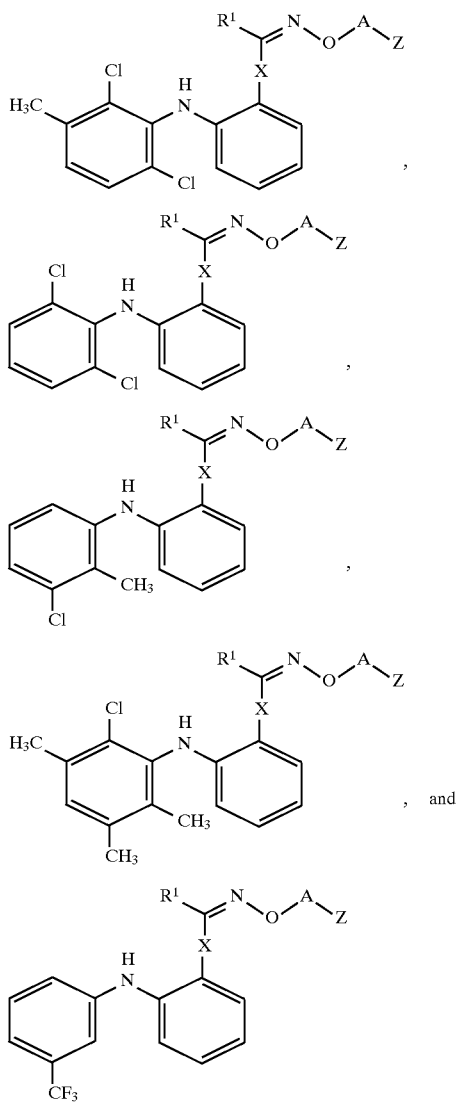

wherein R¹, X, A, and Z are defined above.

Still yet more preferred compounds of this invention have the structure immediately above wherein A is alkylene of one to six carbon atoms and Z is selected from the group consisting of —CH(OH)—CH₂OH, —CH(OH)—CH₂—CH₂OH, and —CH(OH)—CH(OH)—CH₂OH.

Compounds representative of this embodiment include, but are not limited to

2-[(2,6-dichloro-3-methylphenyl)amino]benzaldehyde-O-(2-hydroxyethyl) oxime,
2-[(2,6-dichloro-3-methylphenyl)amino]benzaldehyde-O-(3-hydroxypropyl) oxime,
2-[(2,6-dichloro-3-methylphenyl)amino]benzaldehyde-O-[1-(2,3-dihydroxypropyl)] oxime,
2-[2-[(2,6-dichlorophenyl)amino]phenyl]acetaldehyde-O-(2-hydroxyethyl) oxime,
2-[2-[(2,6-dichlorophenyl)amino]phenyl]acetaldehyde-O-(3-hydroxypropyl) oxime, and
2-[2-[(2,6-dichlorophenyl)amino]phenyl]acetaldehyde-O-[1-(2,3-dihydroxypropyl) oxime.

The most preferred compounds of the present invention have the structure immediately above wherein A is alkylene of one to six carbon atoms, and Z is —COOR⁴ wherein R⁴ is hydrogen or a pharmaceutically acceptable cation.

Compounds representative of the most preferred embodiment include, but are not limited to 2-[(2,6-dichloro-3-methylphenyl)amino]benzaldehyde-O-carboxymethyl oxime,
2-[(2,6-dichloro-3-methylphenyl)amino]benzaldehyde-O-(3-carboxyethyl) oxime,
2-[(2,6-dichloro-3-methylphenyl)amino]phenyl}acetophenone-O-carboxymethyl oxime,
2-{[(2,6-dichloro-3-methylphenyl)amino]phenyl} phenyl ketone-O-carboxymethyl oxime,
2-[(2,6-dichloro-3-methylphenyl)amino]phenylmethyl ketone-O-carboxymethyl oxime,
2-[2-[(2,6-dichlorophenyl)amino]phenyl]acetaldehyde-O-carboxymethyl oxime,
2-[2-[(2,6-dichlorophenyl)amino]phenyl]acetaldehyde-O-carboxyethyl oxime,
[2-[(2,6-dichlorophenyl)amino]benzyl]methyl ketone-O-carboxymethyl oxime,
2-[(3-chloro-2-methylphenyl)amino]benzaldehyde-O-carboxymethyl oxime,
2-[(2,3-dimethylphenyl)amino]benzaldehyde-O-carboxymethyl oxime,
2-[(3-trifluoromethylphenyl)amino]benzaldehyde-O-carboxymethyl oxime, and
2-[(2,6-dichloro-3-methylphenyl)amino]benzaldehyde-O-(2-acetaldehyde oxime) oxime.

Prostaglandin Inhibition Determination

Inhibition of prostaglandin biosynthesis was evaluated in recombinant human PGHS-1 and PGHS-2 enzyme assays. Representative compounds dissolved in DMSO (3.3% v/v) were preincubated with microsomes from recombinant human PGHS-1 or PGHS-2 expressed in the baculovirus/Sf9 cell system (Gierse, J. K., Hauser, S. D., Creely, D. P., Koboldt, C., Rangwala, S., H., Isakson, P. C., and Seibert, K. Expression and selective inhibition of the constituitive and inducible forms of cyclooxygenase Biochem J. 1995, 305: 479.), together with the cofactors phenol (2 mM) and hematin (1 μM) for 60 minutes prior to the addition of 10 μM arachidonic acid. The reaction was allowed to run for 2.5 minutes at room temperature prior to quenching with HCl and neutralization with NaOH. PGE₂ production in the presence and absence of the drug was determined by EIA analysis. The EIA was conducted in 96 well microtiter plates (Nunc Roskilde, Denmark) and optical density measured using a microplate reader (Vmax, Molecular Devices Corp., Menlo Park, Calif.). EIA reagents for prostaglandin determination were purchased from Perseptive Diagnostics, Cambridge, Mass. PGE₂ levels were measured against standards prepared in the same milieu. The immunoassays were conducted as recommended by the manufacturer.

The compounds of this invention inhibit prostaglandin biosynthesis as shown by the data for the representative compounds in Table 1.

TABLE 1

In Vitro Inhibitory Potencies Against Human Recombinant PGHS-1 and PGHS-2

| Example | PGHS-1 IC$_{50}$ ($\mu$M) | PGHS-2 IC$_{50}$ ($\mu$M) |
|---------|---------------------------|---------------------------|
| 1 | 0.85 | 0.022 |
| 5 | 27% @ 1.0 $\mu$M | 64% @ 1.0 $\mu$M |

Pharmaceutical Compositions

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like, Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g. two to four separate doses per day.

Preparation of Compounds of this Invention

The compounds of this invention can be prepared by representative methods described as follows. The known fenamates (Scherrer, R. A. Fenamic acids, in "Anti-inflammatory and anti-rheumatic drugs", Vol II, Rainsford, K. D. ed., CRC Press, Boca Raton, Fla., 1985, Chapter 4, pp 65–85) serve as the starting material for the preparation of the compounds of this invention. Known fenamates include: meclofenamic acid, mefenamic acid, flufenamic acid and tolfenamic acid.

Alternative fenamate templates with various $Y_n$ can be prepared by known methods (Scherrer, R. A. Fenamic acids, in "Anti-inflammatory and anti-rheumatic drugs", Vol II, Rainsford, K. D. ed., CRC Press, Boca Raton, Fla., 1985, Chapter 4, pp 65–85).

General synthetic routes to the compounds of this invention are outlined in Schemes 1a and 1b. According to Scheme 1a, the carboxylate group of the fenamate is converted to the N-methoxy-N-methylamide II, for example using N,O-dimethylhydroxylamine hydrochloride, carbon tetrabromide, triphenylphosphine, and pyridine. The amide is then selectively reduced to the aldehyde III using diisobutylaluminum hyride. Reaction of the aldehyde intermediate III with the requisite hydroxylamine IV provides the desired oxime derivatives in which $R_1$ is H.

Alternatively, the fenamate can be selectively reduced to the aldehyde III by known methods such as diisobutylaluminum hydride, or the requisite aldehyde intermediate can be prepared by reduction of the carboxylate group to the corresponding hydroxy intermediate V using, for example, lithium aluminum hydride, followed by oxidation to the desired aldehyde intermediate III by standard methods such as the Swern oxidation (Swern, et al., *J. Org. Chem.*, 1978, 43, 2480). The oxime derivative is then prepared as desribed above.

Scheme 1a

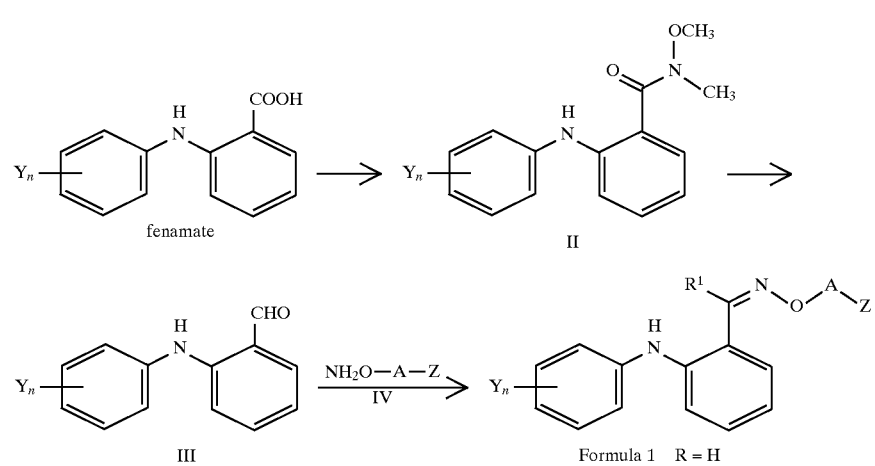

-continued

Scheme 1b

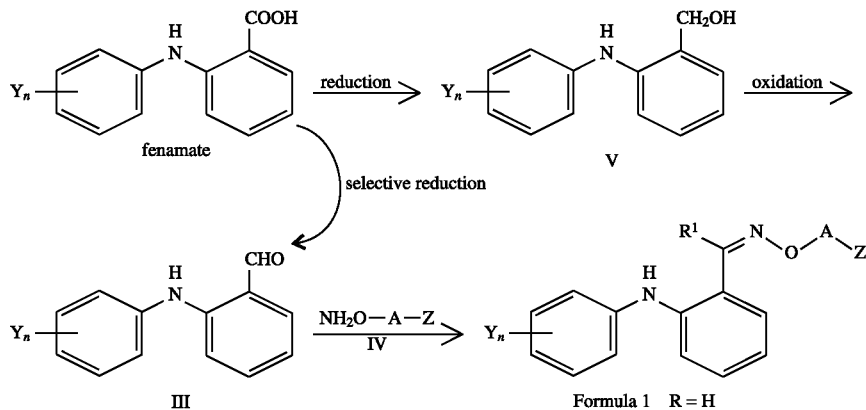

Compounds of the present invention in which $R^1$ is other than hydrogen are prepared as outlined in Scheme 2. Reaction of amide II with a an organometallic reagent of formula $R^1M$ provides ketone VII in a single step. Especially preferred nucleophilic species are organolithium reagents of formula $R^1Li$ and Grignard reagents of formula $R^1MgX$ wherein X is Br or Cl. Reaction of the aldehyde intermediate III with a nucleophilic species derived from $R^1$ provides the hydroxy intermediate VI. Preferred nucleophilic species have the formula $R^1Li$ or $R^1MgX$ wherein X is Br or Cl. Oxidation of the hydroxy intermediate VI, for example using Swern oxidation conditions provides the ketone VII. Reaction of VII with the requisite hydroxylamine derivative IV as described in Scheme 1 provides the desired oxime derivative.

Scheme 2

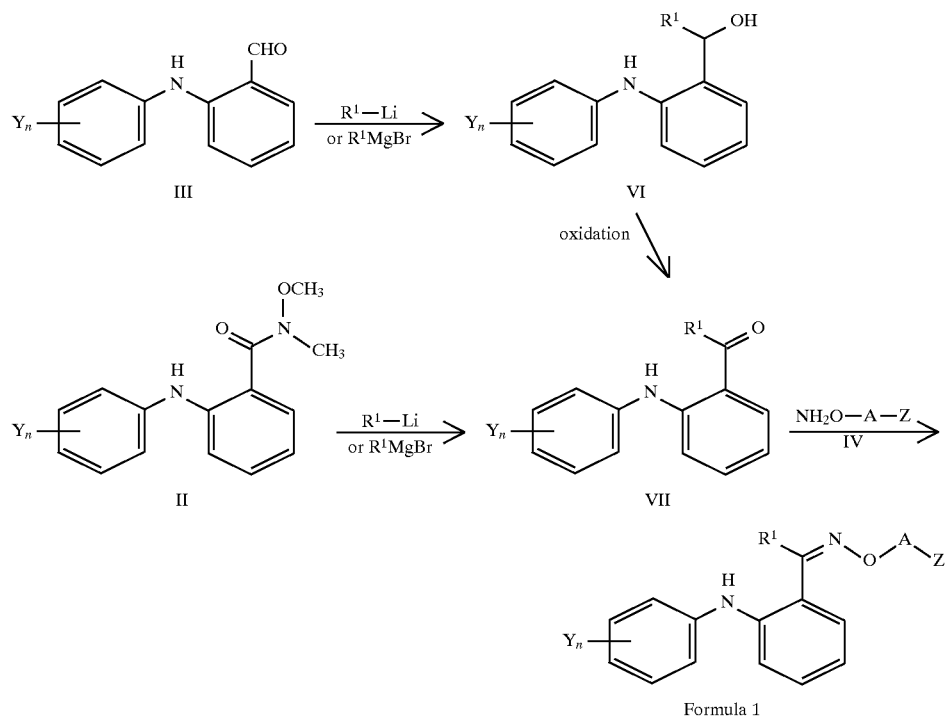

The hydroxylamine intermediate $NH_2O$—A—Z is prepared reaction of the alcohol HO—A—Z with N-hydroxyphthalimide, triphenylphosphine, and diethyl- or diisopropylazodicarboxylate to form the N-phthaloylhydroxylamine derivative, which is converted to the hydroxylamine IV by reaction with hydrazine.

Scheme 3

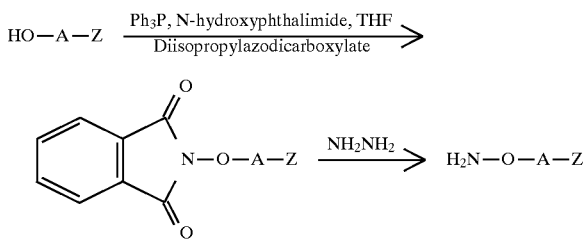

The foregoing may be better understood by reference to the following examples which are provided for illustration and not intended to limit the scope of the inventive concept. The compounds of this invention consist of E and Z isomers of the oxime function and R and S enantiomers when there is an asymmetric carbon center. The individual or mixtures of isomers and/or enantiomers are considered as part of this invention.

EXAMPLE 1

Preparation of 2-[(2,6-dichloro-3-methylphenyl)amino] benzaldehyde-O-carboxymethyl oxime

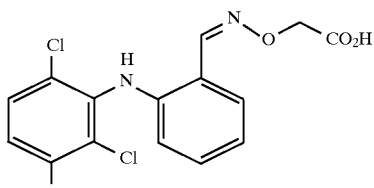

Step 1: N-methoxy-N-methyl-2-[(2,6-dichloro-4-methylphenyl)amino]benzamide.

A mixture in dry dichloromethane (135 mL) of 2-[(2,6-dichloro-4-methylphenyl)amino]benzoic acid (meclofenamic acid) (7.0 g, 23.6 mmol), N,O-dimethylhydroxylamine hydrochloride (5.0 g, 51.9 mmol), carbon tetrabromide (17.2 g, 51.9 mmol), triphenylphosphine (13.6 g, 51.9 mmol), and pyridine (10 mL) was stirred at ambient temperature for 48 hours. The reaction mixture was poured into 10% HCl (100 mL) and extracted with ethyl acetate (3×200 mL). The combined organic layers were washed with water and brine, dried over $MgSO_4$, filtered, and evaporated in vacuo. Purification by chromatography on silica gel (9:1 hexane/ethyl acetate) provided 7.98 g (99%) of 2-[(2,6-dichloro-3-methylphenyl)amino]benzaldehyde as a colorless solid.

Step 2: 2-[(2,6-dichloro-3-methylphenyl)amino] benzaldehyde.

To a magnetically stirred 0° C. solution in dry THF (25 mL) of N-methoxy-N-methyl-2-[(2,6-dichloro-4-methylphenyl)amino]benzamide (3.8 g, 11.2 mmol), prepared as in step 1, was added dropwise diisobutylaluminum hydride (1.0M in THF, 24.6 mL) and the reaction mixture was stirred at ambient temperature for 16 hours. Methanol (5 mL) was added dropwise and the mixture was stirred for 15 minutes until a white precipitate had formed. The reaction mixture was concentrated, the residue was taken up in methanol (10 mL), the insoluble white solid was filtered, and the filtrate was evaporated in vacuo and then purified by chromatography on silica gel (5:1 hexane/$CH_2Cl_2$) to provide 2-[(2,6-dichloro-3-methylphenyl)amino]benzaldehyde (1.98 g; 63%) and over reduced alcohol side product (0.70 g; 22%).

Step 3: 2-[(2,6-dichloro-3-methylphenyl)aminophenyl] benzaldehyde-O-carboxymethyl oxime.

A mixture in ethanol (20 mL) of 2-[(2,6-dichloro-3-methylphenyl)amino]benzaldehyde (1.10 g, 3.9 mmol), prepared as in step 1 above, O-carboxymethyl hydroxylamine hemihydrochloride (0.945 g, 4.3 mmol), and pyridine (8 mL) was stirred at reflux for 18 hours. After cooling the reaction was concentrated and the residue was acidified to pH 2 with 10% aqueous citric acid. The mixture was then extracted with ethyl acetate (4×100 mL), the combined organic layers were washed with water and brine, dried over $MgSO_4$, filtered, evaporated in vacuo. Purification by chromatography on silica gel (9:1 hexane/ethyl acetate, followed by 9:1 $CH_2Cl_2/CH_3OH$) and crystallization from ethyl acetate-ether-hexane gave 2-[(2,6-dichloro-3-methylphenyl) aminophenyl]benzaldehyde-O-carboxymethyl oxime (751 mg, 54%). mp 129°–130° C.; $^1H$ NMR (300 MHz, DMSO-$d_6$)δ2.37 (s, 3H), 4.70 (s, 2H), 6.21 (d, J=9 Hz, 1H), 6.83 (t, J=7.5 Hz, 1H), 7.17 (t, J=7.5 Hz, 1H), 7.33 (d, J=9 Hz, 1H), 7.45 (d, J=9 Hz, 1H), 7.50 (d, J=9 Hz, 1H), 8.58 (s, 1H), 8.73 (s, 1H), 12.81 (broad s, 1H); MS (DCI-$NH_3$) m/z 353 $(M+H)^+$, 370 $(M+NH_4)^+$. Anal. Calcd for $C_{16}H_{14}Cl_2N_2O_3$: C, 54.41, H, 4.00, N, 7.93. Found: C, 54.13, H, 3.92; N, 7.69.

EXAMPLE 2

Preparation of 2-[(2,6-dichloro-3-methylphenyl)amino] benzaldehyde-O-(3-carboxyethyl) oxime

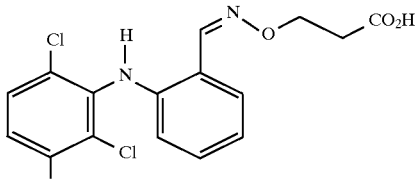

A mixture in ethanol (9 mL) of 2-[(2,6-dichloro-3-methylphenyl)amino]benzaldehyde (0.50 g, 1.78 mmol) prepared as in Example 1, steps 1–2,O-(propionic acid) hydroxylamine hydrochloride (0.483 g, 1.96 mmol), and pyridine (4 mL) was stirred at reflux for 5 hours. After cooling the reaction was concentrated and the residue was acidified to pH 2 with 10% aqueous citric acid. The mixture was then extracted with ethyl acetate (4×50 mL), and the combined organic layers were washed with water and brine, dried over $MgSO_4$, filtered, and evaporated in vacuo. Purification by chromatography on silica gel (20:1 $CH_2Cl_2/CH_3OH$) and crystallization from ethyl acetate-hexane gave 2-[(2,6-dichloro-3-methylphenyl)amino]benzaldehyde-O-(3-carboxyethyl) oxime (630 mg, 96%). mp 110°–111° C.; $^1H$ NMR (300 MHz, DMSO-$d_6$)δ2.39 (s, 3H), 2.56 (t, J=6 Hz, 2H), 4.33 (t, J=6 Hz, 2H), 6.21 (d, J=9 Hz, 1H), 6.83 (t, J=7.5 Hz, 1H), 7.17 (t, J=7.5 Hz, 1H), 7.35 (d, J=9 Hz, 1H), 7.43 (d, J=9 Hz, 1H), 7.52 (d, J=9 Hz, 1H), 8.50 (s, 1H), 8.81 (s, 1H), 12.31 (s, 1H); MS (DCI-$NH_3$) m/z 366 $(M+H)^+$. Anal. Calcd for $C_{17}H_{16}Cl_2N_2O_3$: C, 55.60, H, 4.39, N, 7.63. Found: C, 55.36, H, 4.32; N, 7.55.

EXAMPLE 3

Preparation of 2-[(2,6-dichloro-3-methylphenyl)amino] benzaldehyde-O-(2-hydroxyethyl) oxime

17

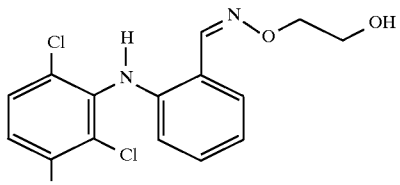

The title compound is prepared by the reduction of 2-[(2,6-dichloro-3-methylphenyl)aminophenyl]benzaldehyde-O-carboxymethyl oxime, prepared as in Example 1, with diborane-THF.

EXAMPLE 4
Preparation of 2-[(2,6-dichloro-3-methylphenyl)amino]benzaldehyde-O-(3-hydroxypropyl) oxime

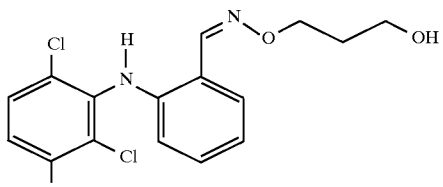

The title compound was prepared in 74% yield by the reduction of 2-[(2,6-dichloro-3-methylphenyl)amino]benzaldehyde-O-(3-carboxyethyl) oxime, prepared as in Example 2, with diborane-THF and chromatography on silica gel (25% ethyl acetate/hexanes). $^1$H NMR (300 MHz, DMSO-$d_6$) $\delta$ 1.53 (m, 2H), 2.38 (s, 3H), 3.51 (m, 2H), 4.19 (t, 2H), 4.50 (t, 1H), 6.22 (m, 1H), 6.32 (m, 1H), 7.16 (m, 1H), 7.34 (d, 1H); 7.43 (m, 1H), 7.52 (m, 1H), 8.49 (s, 1H), 8.88 (bs, 1H); MS(DCI-NH$_3$) m/z 353 (M+H)$^+$. Anal. Calcd. for $C_{17}H_{18}Cl_2N_2O_2$: C, 57.80; H, 5.14; N, 7.93. Found: C, 57.56; H, 5.14; N, 7.80.

EXAMPLE 5
Preparation of 2-[(2,6-dichloro-3-methylphenyl)amino]benzaldehyde-O-[1-(2,3-dihydroxypropyl)] oxime

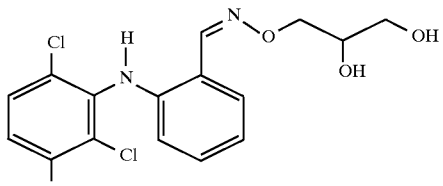

Step 1: 2-[(2,6-dichloro-3-methylphenyl)amino]benzaldehyde-O-allyl oxime.

A solution in 3:1 ethanol-pyridine of 2-[(2,6-dichloro-3-methylphenyl)amino]benzaldehyde, prepared as in Example 1, steps 1–2, and O-allyl hydroxylamine(1.3 eq) was heated at reflux for 2 days. The reaction mixture was poured into ethyl acetate and the mixture was extracted with 10% aqueous HCl. Chromatography on silica gel (20% CH$_2$Cl$_2$/hexanes) gave 2-[(2,6-dichloro-3-methylphenyl)amino]benzaldehyde-O-allyl oxime (1.13 g, 94%).

Step 2: 2-[(2,6-dichloro-3-methylphenyl)amino]benzaldehyde-O-[1-(2,3-dihydroxypropyl)] oxime.

To a 0° C. solution in 10:1 acetone-H$_2$O (10 mL) of the 2-[(2,6-dichloro-3-methylphenyl)amino]benzaldehyde-O-allyl oxime prepared in step 1 was added OsO$_4$ (0.01 mL of a 25% t-BuOH solution, catalytic) and N-methylmorpholine N-oxide (2.5 eq). The reaction mixture was stirred for 24 hours at room temperature and then was diluted with water and extracted with ethyl acetate. The organic phase was dried over MgSO4, filtered, and concentrated in vacuo. Chromatography on silica gel (65% ethyl acetate/hexanes) gave 2-[(2,6-dichloro-3-methylphenyl)amino]benzaldehyde-O-[1-(2,3-dihydroxypropyl)] oxime (0.34 g, 90%) as a white foam. $^1$H NMR (300 MHz, DMSO-$d_6$) $\delta$ 2.40 (s, 3H), 3.40 (m, 2H), 3.78 (m, 1H), 3.51 (m, 2H), 4.04 (m, 1H), 4.17 (m, 1H), 4.59 (t, 1H), 4.83 (d, 1H), 6.20 (d, 1H), 6.82 (t, 1H), 7.15 (m, 1H), 7.35 (d, 1H), 7.43 (m, 1H), 7.53 (m, 1H), 8.50 (s, 1H), 8.87 (bs, 1H); MS(DCI-NH$_3$) m/z 386 (M+NH$_4$)$^+$, 369 (M+H)$^+$. Anal. Calcd. for $C_{17}H_{18}Cl_2N_2O_3$: C, 55.30; H, 4.91; N, 7.59. Found: C, 55.21; H, 4.88; N, 7.34.

EXAMPLE 6
Preparation of 2-[(2,6-dichloro-3-methylphenyl)amino]benzaldehyde-O-(5-tetrazolylmethyl) oxime

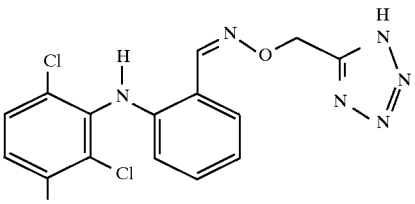

The title compound is prepared by the reaction of 2-[(2,6-dichloro-3-methylphenyl)amino]benzaldehyde, prepared as in Example 1, steps 1–2, with O-(5-tetrazolylmethyl) hydroxylamine.

EXAMPLE 7
Preparation of 2-[(2,6-dichloro-3-methylphenyl)amino]benzaldehyde-O-(aceto-2-hydroxyethylamide) oxime

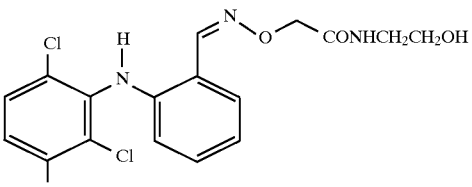

The title compound is prepared by the reaction of 2-[(2,6-dichloro-3-methylphenyl)aminophenyl]benzaldehyde-O-carboxymethyl oxime, prepared as in Example 1, with oxalyl chloride followed by the addition of ethanolamine.

EXAMPLE 8
Preparation of 2-[(2,6-dichloro-3-methylphenyl)amino]benzaldehyde-O-(acetohydroxamic acid) oxime

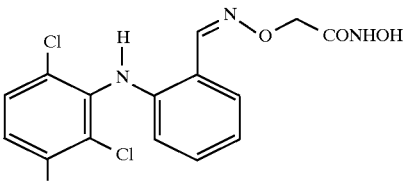

The title compound is prepared by the reaction of 2-[(2,6-dichloro-3-methylphenyl)aminophenyl]benzaldehyde-O-carboxymethyl oxime, prepared as in Example 1, with oxalyl chloride followed by the addition of hydroxylamine.

EXAMPLE 9
Preparation of 2-[(2,6-dichloro-3-methylphenyl)amino]phenyl}acetophenone-O-carboxymethyl oxime

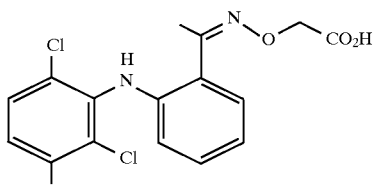

Step 1: 1-{2-[(2,6-dichloro-3-methylphenyl)amino]phenyl}ethanol.

The desired compound was prepared by the reaction of 2-[(2,6-dichloro-3-methylphenyl)amino]benzaldehyde, prepared as in Example 1, steps 1–2, with excess $CH_3MgBr$.

Step 2: Preparation of 2-[(2,6-dichloro-3-methylphenyl)amino]acetophenone.

The desired compound was prepared by oxidation of 1-{2-[(2,6-dichloro-3-methylphenyl)amino]phenyl}ethanol, prepared as in step 1, with Jones reagent.

Step 3: 2-[(2,6-dichloro-3-methylphenyl)amino]phenyl}acetophenone-O-carboxymethyl oxime.

The desired compound was prepared (66% yield after chromatography on silica gel; 25% ethyl acetate/hexanes) according to the method of Example 1, step 3, except substituting 2-[(2,6-dichloro-3-methylphenyl)amino]acetophenone, prepared as in step 2, for 2-[(2,6-dichloro-3-methylphenyl)amino]benzaldehyde. mp 152°–152.5° C.; $^1H$ NMR (300 MHz, DMSO-$d_6$) δ2.45 (s, 3H), 2.47 (s, 3H), 4.72 (s, 2H), 6.22 (m, 1H), 6.83 (m, 1H), 7.13 (m, 1H), 7.27 (m, 1H), 7.48 (m, 2H), 9.03 (s, 1H), 12.83 (bs, 1H); MS(DCI-$NH_3$) m/z 367 (M+H)$^+$. Anal. Calcd. for $C_{17}H_{16}Cl_2N_2O_3$: C, 55.60; H, 4.39; N, 7.62. Found: C, 55.01; H, 4.07; N, 7.62.

EXAMPLE 10

Preparation of 2-{[(2,6-dichloro-3-methylphenyl)amino]phenyl}phenyl ketone-O- carboxymethyl oxime

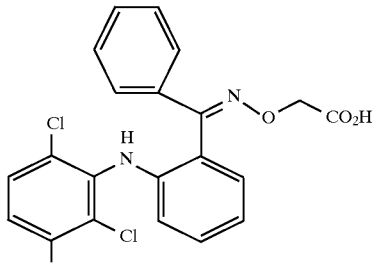

The desired compound is prepared according to the method of Example 9, except substituting phenyllithium for methylmagnesium bromide.

EXAMPLE 11

Preparation of 2-[(2,6-dichloro-3-methylphenyl)amino]phenylmethyl ketone-O-carboxymethyl oxime

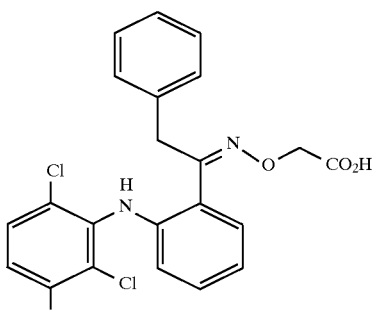

The desired compound is prepared according to the method of Example 9, except substituting phenylmethylmagnesium chloride for methylmagnesium bromide.

EXAMPLE 12

Preparation of 2-[2-[(2,6-dichlorophenyl)amino]phenyl]acetaldehyde-O-carboxymethyl oxime

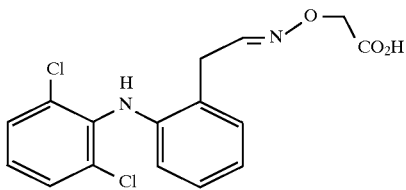

The title compound is prepared by the method of Example 1, except substituting diclofenac for meclofenamic acid.

EXAMPLE 13

Preparation of 2-[2-[(2,6-dichlorophenyl)amino]phenyl]acetaldehyde-O-carboxyethyl oxime

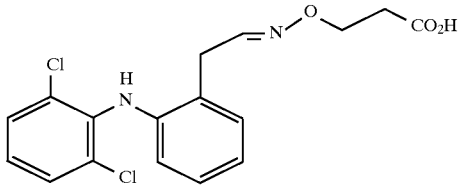

The title compound is prepared by the method of Example 2, except substituting diclofenac for meclofenamic acid.

EXAMPLE 14

Preparation of 2-[2-[(2,6-dichlorophenyl)amino]phenyl]acetaldehyde-O-(2-hydroxyethyl) oxime

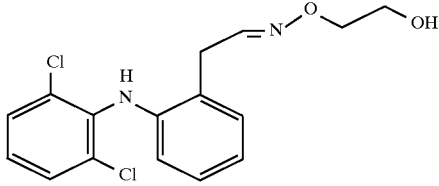

The title compound is prepared reduction of 2-[2-[(2,6-dichlorophenyl)amino]phenyl]ethyl-O-carboxymethyl oxime, prepared as in Example 12, with diborane-THF.

EXAMPLE 15

Preparation of 2-[2-[(2,6-dichlorophenyl)amino]phenyl]acetaldehyde-O-(3-hydroxypropyl) oxime

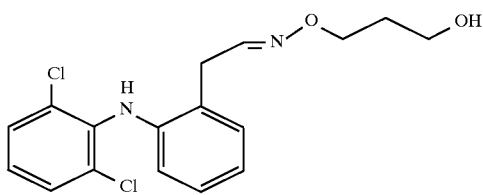

The title compound is prepared by the method of Example 4, except substituting diclofenac acid for meclofenamic acid.

EXAMPLE 16
Preparation of 2-[2-[(2,6-dichlorophenyl)amino]phenyl]acetaldehyde-O-[1-(2,3-dihydroxypropyl) oxime

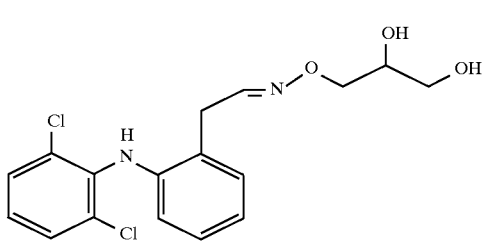

The desired compound is prepared according to the method of Example 5, except substituting diclofenac for meclofenamic acid.

EXAMPLE 17
Preparation of 2-[2-[(2,6-dichlorophenyl)amino]phenyl]acetaldehyde-O-(5-tetrazolylmethyl) oxime

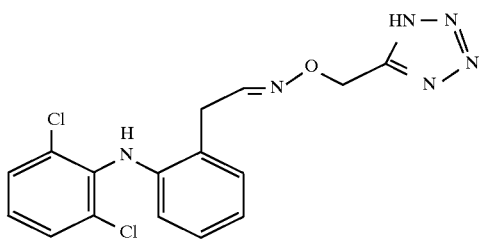

The desired compound is prepared according to the method of Example 6, except substituting diclofenac for meclofenamic acid.

EXAMPLE 18
Preparation of 2-[2-[(2,6-dichlorophenyl)amino]phenyl]acetaldehyde-O-(acetohydroxamic acid) oxime

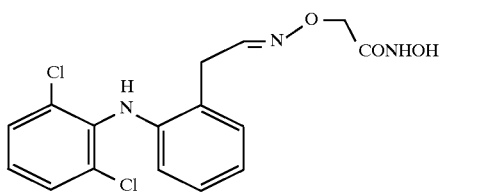

The desired compound is prepared according to the method of Example 8, except substituting diclofenac for meclofenamic acid.

EXAMPLE 19
Preparation of [2-[(2,6-dichlorophenyl)amino]benzl]methyl ketone-O-carboxymethyl oxime

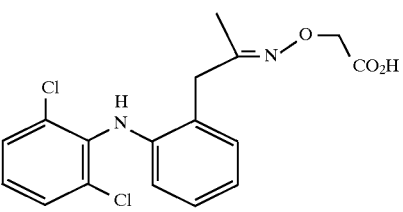

The desired compound is prepared according to the method of Example 9, except substituting diclofenac for meclofenamic acid.

EXAMPLE 20
Preparation of 2-[(3-chloro-2-methylphenyl)amino]benzaldehyde-O-carboxymethyl oxime

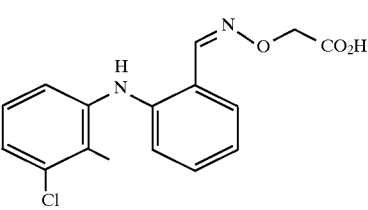

The title compound is prepared by the method of Example 1, except substituting tofenamic acid for meclofenamic acid.

EXAMPLE 21
Preparation of 2-[(2,3-dimethylphenyl)amino]benzaldehyde-O-carboxymethyl oxime

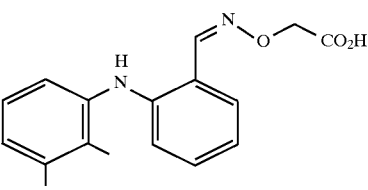

The title compound is prepared by the method of Example 1, except substituting mefenamic aicd for meclofenamic acid.

EXAMPLE 22
Preparation of 2-[(3-trifluoromethylphenyl)amino]benzaldehyde-O-carboxymethyl oxime

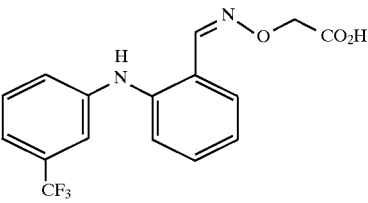

The title compound is prepared by the method of Example 1, except substituting flufenamic acid for meclofenamic acid.

EXAMPLE 23
Preparation of 2-[(2,6-dichloro-3-methylphenyl)amino]benzaldehyde-O-(2-acetaldehyde oxime) oxime

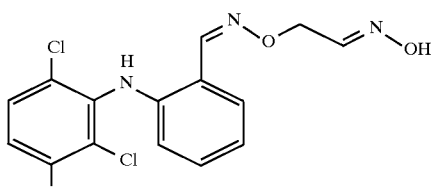

To a solution in THF of 2-[(2,6-dichloro-3-methylphenyl)amino]benzaldehyde-O-allyl oxime (2.0 mm01), prepared as in Example 5, step 1, was added $OsO_4$ (20 ml, 2.5% solution in t-BuOH) and $NaIO_4$ (10 mmol, in 2 mL $H_2O$). The mixture was stirred for 1 hour. The reaction mixture was filtered and filtrate diluted with ethyl acetate and washed with water and brine, dried over $MgSO_4$, filtered, and concentrated in vacuo. The residue was dissolved in ethanol-pyridine(2:1) and hydroxylamine hydrochloride (3.2 mmol) was added. The reaction was heated to reflux for 5 hours. The mixture was extracted with ethyl acetate and 10% HCl. Purification by column chromatography on silica gel (10% ethyl acetate/hexanes) gave 2-[(2,6-dichloro-3-methylphenyl)amino]benzaldehyde-O-(2-acetaldehyde oxime) oxime (0.084 g, 15%) as a white solid that was a 1:1 mixture of E:Z oximes. mp 124°–126° C.; $^1$H NMR (300 MHz, DMSO-$d_6$)δ2.34 (s, 3H), 4.67 (m, 1H), 4.88 (m, 1H), 6.17 (m, 2H), 6.78 (m, 1H), 6.93 (m, 0.5H), 7.15 (m, 1H), 7.31 (d, 1H), 7.41 (m, 1H), 7.48 (m, 1.5H), 8.52 (m, 0.5H), 8.56 (m, 0.5H), 8.70 (bs, 1H), 11.00 (s, 0.5H), 11.19 (s, 0.5H); MS(DCI-$NH_3$) m/z 352 (M+H)$^+$. Anal. Calcd. for $C_{16}H_{15}Cl_2N_3O_2$: C, 51.91; H, 3.63; N, 11.35. Found: C, 51.70; H, 3.52; N, 11.01.

We claim:

1. A compound having the formula:

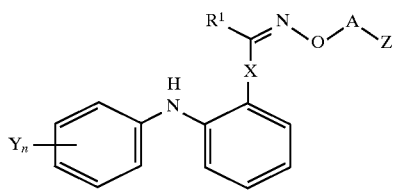

or a pharmaceutically acceptable salt thereof wherein
Y is selected from the group consisting of
halogen,
alkyl of one to six carbon atoms, and
haloalkyl of one to six carbon atoms, and
n is 0, 1, 2, or 3;
A is selected from the group consisting of
(a) alkylene of one to six carbon atoms,
(b) alkylene of one to six carbon atoms substituted with one or two substituents selected from the group consisting of
—$OR^2$,
—CN,
—$NO_2$, and
—$COOR^2$,
(c) cycloalkylene of three to eight carbon atoms,
(d) cycloalkylene of three to eight carbon atoms substituted with one or two substituents independently selected from
alkyl of one to six carbon atoms,
—$OR^2$,
—CN,
—$NO_2$, and
—$COOR^2$,
(e) cycloalkylene of three to eight carbon atoms wherein one or two of the carbon atoms is replaced with one or two heteroatomsindependently selected from O, S, and N,
(f) cycloalkylene of three to eight carbon atoms wherein one or two of the carbon atoms is replaced with one or two heteroatoms independently selected from O, S, and N, and the ring contains one or two substituents independently selected from
alkyl of one to six carbon atoms,
—$OR^2$,
—CN,
—$NO_2$, and
—$COOR^2$,
(g) alkenylene of two to six carbon atoms,
(h) alkenylene of two to six carbon atoms substituted with one or two substituents selected from the group consisting of
—$OR^2$,
—CN,
—$NO_2$, and
—$COOR^2$,
(i)

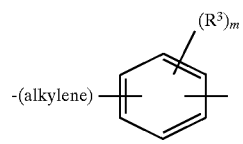

wherein m is 0, 1, 2, or 3, and $R^3$, which may be the same or different at each occurrence, is selected from the group consisting of
—$OR^2$
—CN,
—$NO_2$,
—$COOR^2$,
halogen,
alkyl of one to six carbon atoms,
haloalkyl of one to six carbon atoms, and
alkoxy of one to six carbon atoms;
X is absent or is alkylene of one to six carbon atoms;
Z is selected from the group consisting of
(a) hydrogen,
(b) COM wherein M is selected from the group consisting of
—$OR^4$ wherein $R^4$ is selected from the group consisting of
a pharmaceutically acceptable cation,
hydrogen,
alkyl of one to six carbon atoms,
phenyl,
phenyl substituted one, two or three substituents selected from
halogen,
alkyl of one to six carbon atoms, haloalkyl of one to six carbon atoms,
alkoxy of one to six carbon atoms, and

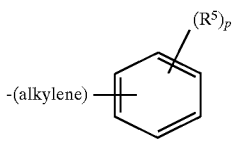

wherein p is 0, 1, 2, or 3, and $R^5$, which may be the same or different at each occurrence, is selected from
halogen,
alkyl of one to six carbon atoms,
haloalkyl of one to six carbon atoms, and
alkoxy of one to six carbon atoms, and
—$NR^6R^7$ wherein $R^6$ and $R^7$ are independently selected from
hydrogen,
alkyl of one to six carbon atoms,
hydroxyalkyl of one to six carbon atoms, and
hydroxy; and
a pharmaceutically acceptable metabolically cleavable group,
(c) —$OR^2$,
(d) tetrazolyl
(e) —$CH(OR^2)$—$CH_2OR^8$,
(f) —$CH(OR^2)$—$CH_2$—$CH_2OR^8$, and
(g) —$CH(OR^2)$—$CH(OR^8)$—$CH_2OR^9$, and
(h) =N—$OR^2$; and
$R^1$, $R^2$, $R^8$, and $R^9$ are independently selected at each occurrence from the group consisting of
(a) hydrogen,
(b) alkyl of one to six carbon atoms,
(c) phenyl,
(d) phenyl substituted one, two or three substituents selected from
halogen,
alkyl of one to six carbon atoms,
haloalkyl of one to six carbon atoms, and
alkoxy of one to six carbon atoms, and

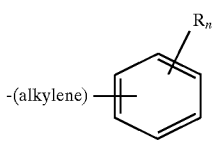

wherein m is 0, 1, 2, or 3, and R, which may be the same or different at each occurrence, is selected from halogen,
alkyl of one to six carbon atoms,
haloalkyl of one to six carbon atoms, and
alkoxy of one to six carbon atoms.

2. A compound or pharmaceutically acceptable salt thereof as defined by claim 1 wherein A is alkylene of one to six carbon atoms.

3. A compound or pharmaceutically acceptable salt thereof as defined by claim 2 wherein Z is —$COOR^4$ wherein $R^4$ is hydrogen or a pharmaceutically acceptable cation.

4. A compound or pharmaceutically acceptable salt thereof as defined by claim 2 wherein Z is selected from the group consisting of
—CH(OH)—$CH_2OH$,
—CH(OH)—$CH_2$—$CH_2OH$, and
—CH(OH)—CH(OH)—$CH_2OH$.

5. A compound or pharmaceutically acceptable salt thereof as defined by claim 1 selected from the group consisting of

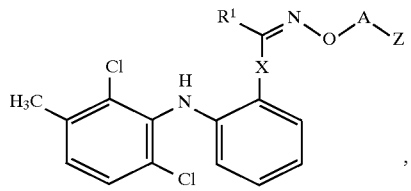,

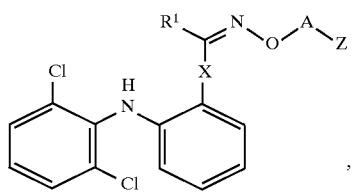,

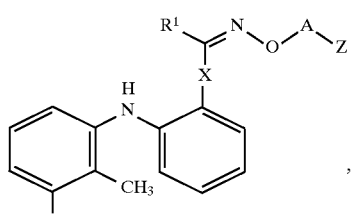,

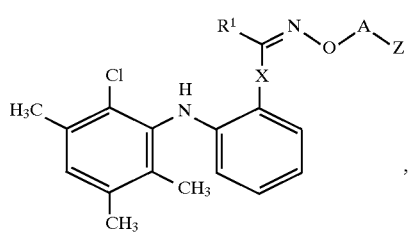, and

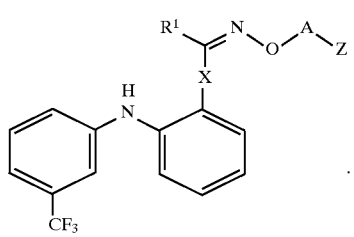.

6. A compound or pharmaceutically acceptable salt thereof as defined by claim 5 wherein A is alkylene of one to six carbon atoms.

7. A compound or pharmaceutically acceptable salt thereof as defined by claim 6 wherein Z is —$COOR^4$ wherein $R^4$ is hydrogen or a pharmaceutically acceptable cation.

8. A compound or pharmaceutically acceptable salt thereof as defined by claim 6 wherein Z is selected from the group consisting of
—CH(OH)—$CH_2OH$,
—CH(OH)—$CH_2$—$CH_2OH$, and
—CH(OH)—CH(OH)—$CH_2OH$.

9. A compound or pharmaceutically acceptable salt thereof as defined by claim 1 selected from the group consisting of
2-[(2,6-dichloro-3-methylphenyl)amino]benzaldehyde-O-carboxymethyl oxime,
2-[(2,6-dichloro-3-methylphenyl)amino]benzaldehyde-O-(3-carboxyethyl) oxime, 2-[(2,6-dichloro-3-methylphenyl)amino]benzaldehyde-O-(2-hydroxyethyl) oxime, 2-[(2,6-dichloro-3-methylphenyl)amino]benzaldehyde-O-(3-hydroxypropyl) oxime, 2-[(2,6-dichloro-3-methylphenyl)amino]benzaldehyde-O-[1-(2,3-dihydroxypropyl)] oxime, 2-[(2,6-dichloro-3-methylphenyl)amino]benzaldehyde-O-(5-tetrazolylmethyl) oxime, 2-[(2,6-dichloro-3-methylphenyl)amino]benzaldehyde-O-(aceto-2-hydroxyethylamide) oxime, 2-[(2,6-dichloro-3-methylphenyl)amino]benzaldehyde-O-(acetohydroxamic acid) oxime, 2-[(2,6-dichloro-3-methylphenyl)amino]phenyl}acetophenone-O-carboxymethyl oxime, 2-{[(2,6-dichloro-3-methylphenyl)amino]phenyl}phenyl ketone-O-carboxymethyl oxime, 2-[(2,6-dichloro-3-methylphenyl)amino]phenylmethyl ketone-O-carboxymethyl oxime, 2-[2-[(2,6-dichlorophenyl)amino]phenyl]acetaldehyde-O-carboxymethyl oxime, 2-[2-[(2,6-dichlorophenyl)amino]phenyl]acetaldehyde-O-carboxyethyl oxime, 2-[2-[(2,6-dichlorophenyl)amino]phenyl]acetaldehyde-O-(2-hydroxyethyl) oxime, 2-[2-[(2,6-dichlorophenyl)amino]phenyl]acetaldehyde-O-(3-hydroxypropyl) oxime, 2-[2-[(2,6-dichlorophenyl)amino]phenyl]acetaldehyde-O-[1-(2,3-dihydroxypropyl) oxime, 2-[2-[(2,6-dichlorophenyl)amino]phenyl]acetaldehyde-O-(5-tetrazolylmethyl) oxime, 2-[2-[(2,6-dichlorophenyl)amino]phenyl]acetaldehyde-O-(acetohydroxamic acid) oxime,

[2-[(2,6-dichlorophenyl)amino]benzyl]methyl ketone-O-carboxymethyl oxime,

2-[(3-chloro-2-methylphenyl)amino]benzaldehyde-O-carboxymethyl oxime,

2-[(2,3-dimethylphenyl)amino]benzaldehyde-O-carboxymethyl oxime,

2-[(3-trifluoromethylphenyl)amino]benzaldehyde-O-carboxymethyl oxime, and

2-[(2,6-dichloro-3-methylphenyl)amino]benzaldehyde-O-(2-acetaldehyde oxime) oxime.

10. A compound or pharmaceutically acceptable salt thereof as defined by claim 1 selected from the group consisting of 2-[(2,6-dichloro-3-methylphenyl)amino]benzaldehyde-O-(2-hydroxyethyl) oxime, 2-[(2,6-dichloro-3-methylphenyl)amino]benzaldehyde-O-(3-hydroxypropyl) oxime, 2-[(2,6-dichloro-3-methylphenyl)amino]benzaldehyde-O-[1-(2,3-dihydroxypropyl)] oxime, 2-[2-[(2,6-dichlorophenyl)amino]phenyl]acetaldehyde-O-(2-hydroxyethyl) oxime, 2-[2-[(2,6-dichlorophenyl)amino]phenyl]acetaldehyde-O-(3-hydroxypropyl) oxime, 2-[2-[(2,6-dichlorophenyl)amino]phenyl]acetaldehyde-O-[1-(2,3-dihydroxypropyl) oxime.

11. A compound or pharmaceutically acceptable salt thereof as defined by claim 1 selected from the group consisting of 2-[(2,6-dichloro-3-methylphenyl)amino]benzaldehyde-O-carboxymethyl oxime, 2-[(2,6-dichloro-3-methylphenyl)amino]benzaldehyde-O-(3-carboxyethyl) oxime, 2-[(2,6-dichloro-3-methylphenyl)amino]phenyl}acetophenone-O-carboxymethyl oxime, 2-{[(2,6-dichloro-3-methylphenyl)amino]phenyl}phenyl ketone-O-carboxymethyl oxime, 2-[(2,6-dichloro-3-methylphenyl)amino]phenylmethyl ketone-O-carboxymethyl oxime, 2-[2-[(2,6-dichlorophenyl)amino]phenyl]acetaldehyde-O-carboxymethyl oxime, 2-[2-[(2,6-dichlorophenyl)amino]phenyl]acetaldehyde-O-carboxyethyl oxime,

[2-[(2,6-dichlorophenyl)amino]benzyl]methyl ketone-O-carboxymethyl oxime,

2-[(3-chloro-2-methylphenyl)amino]benzaldehyde-O-carboxymethyl oxime,

2-[(2,3-dimethylphenyl)amino]benzaldehyde-O-carboxymethyl oxime,

2-[(3-trifluoromethylphenyl)amino]benzaldehyde-O-carboxymethyl oxime, and

2-[(2,6-dichloro-3-methylphenyl)amino]benzaldehyde-O-(2-acetaldehyde oxime) oxime.

12. A method for inhibiting prostaglandin biosynthesis in a mammal in need of such treatment comprising administering to the mammal a therapeutically effective amount of a compound of claim 1.

13. A composition for inhibiting prostaglandin biosynthesis comprising a pharmaceutical carrier and a therapeutically effective amount of a compound of claim 1.

* * * * *